United States Patent [19]
Decoster et al.

[11] Patent Number: 6,162,424
[45] Date of Patent: Dec. 19, 2000

[54] COSMETIC COMPOSITIONS CONTAINING A CATIONIC POLYMER OF LOW MOLECULAR MASS AND A SILICONE, AND USES THEREOF

[75] Inventors: Sandrine Decoster, Epinay sur Seine; Bernard Beauquey, Clichy, both of France

[73] Assignee: L'Oréal, Paris, France

[21] Appl. No.: 09/055,760

[22] Filed: Apr. 7, 1998

[30] Foreign Application Priority Data

Apr. 7, 1997 [FR] France .................................. 97 04421

[51] Int. Cl.[7] .................................................. A61K 7/075
[52] U.S. Cl. ............................ 424/70.17; 424/70; 424/12
[58] Field of Search ................................ 424/401, 70.17, 424/70.12; 514/880–81; 510/122–23

[56] References Cited

U.S. PATENT DOCUMENTS

| | | | |
|---|---|---|---|
| 2,258,378 | 10/1941 | Collman . | |
| 2,781,354 | 2/1957 | Mannheimer . | |
| 2,926,161 | 2/1960 | Butler et al. . | |
| 3,912,808 | 10/1975 | Sokol . | |
| 4,693,935 | 9/1987 | Mazurek | 428/352 |
| 4,728,571 | 3/1988 | Clemens et al. | 428/352 |
| 4,943,430 | 7/1990 | Hefford et al. . | |
| 4,972,037 | 11/1990 | Garbe et al. | 526/245 |
| 5,063,044 | 11/1991 | Kohl et al. . | |
| 5,650,383 | 7/1997 | Dubief et al. | 510/122 |

FOREIGN PATENT DOCUMENTS

| | | |
|---|---|---|
| 0 059 428 | 9/1982 | European Pat. Off. . |
| 0 089 749 | 9/1983 | European Pat. Off. . |
| 0 115 252 | 8/1984 | European Pat. Off. . |
| 0 342 834 | 11/1989 | European Pat. Off. . |
| 0 392 320 | 10/1990 | European Pat. Off. . |
| 0 412 704 | 2/1991 | European Pat. Off. . |
| 0 412 707 | 2/1991 | European Pat. Off. . |
| 0 521 748 | 1/1993 | European Pat. Off. . |
| 0 582 152 | 2/1994 | European Pat. Off. . |
| 2 589 476 | 5/1987 | France . |
| 2 641 185 | 7/1990 | France . |
| WO 93/08787 | 5/1993 | WIPO . |
| WO 93/23009 | 11/1993 | WIPO . |
| WO 93/23446 | 11/1993 | WIPO . |
| WO 94/06403 | 3/1994 | WIPO . |
| WO 95/00578 | 1/1995 | WIPO . |
| WO 95/01152 | 1/1995 | WIPO . |
| WO 95/03776 | 2/1995 | WIPO . |
| WO 96/32919 | 10/1996 | WIPO . |

OTHER PUBLICATIONS

English Language Derwent Abstract of FR 2 589 476.

English Language Derwent Abstract of FR 2 641 185.

English Language Derwent Abstract of EP 0 115 252.

*Primary Examiner*—Edward J. Webman
*Attorney, Agent, or Firm*—Finnegan, Henderson, Farabow, Garrett & Dunner, L.L.P.

[57] ABSTRACT

Novel cosmetic compositions comprising, in a cosmetically acceptable medium, at least one silicone and at least one polymer containing units of the diallyldimethylammonium type of low weight-average molecular mass, for example, $5000 < M < 20,000$.

26 Claims, No Drawings

COSMETIC COMPOSITIONS CONTAINING A CATIONIC POLYMER OF LOW MOLECULAR MASS AND A SILICONE, AND USES THEREOF

The present invention relates to novel cosmetic compositions comprising, in a cosmetically acceptable medium, at least one silicone and at least one polymer of low molecular mass containing cationic units.

It is well known that hair which is sensitized (i.e. damaged and/or embrittled) to varying degrees under the action of atmospheric agents or under the action of mechanical or chemical treatments, such as dyeing, bleaching and/or permanent-waving operations, is often difficult to disentangle and to style, and lacks softness.

Thus, in order to improve the cosmetic properties of the above detergent compositions, and more particularly of those which are intended to be applied to sensitized hair (i.e. hair which has been damaged or embrittled, in particular under the chemical action of atmospheric agents and/or of hair treatments such as permanent-waving, dyeing or bleaching operations), it is now common to introduce, into these compositions, additional cosmetic agents known as conditioners, which are intended mainly to repair or limit the harmful or undesirable effects brought about by the various treatments or attacking factors to which hair fibers are subjected more or less repeatedly. Needless to say, these conditioners can also improve the cosmetic behaviour of natural hair.

The conditioners most commonly used to date in shampoos are cationic polymers, silicones and/or silicone derivatives, which give washed dry or wet hair an ease of disentangling, a softness and a smoothness which are all improved when compared with that which can be obtained with the corresponding cleansing compositions in which these polymers are absent. In addition, on sensitized hair, it is known preferably to use a mixture of silicone and cationic polymer. However, the use of cationic polymers for this purpose has various drawbacks. On account of their high affinity for the hair, some of these polymers become deposited to a considerable extent during repeated use, and lead to undesirable effects such as an unpleasant, lank feel, stiffness of the hair and adhesion between the fibers which affects the styling. These drawbacks are accentuated in the case of fine hair, which lacks liveliness and volume.

The aim of the invention is thus to propose cosmetic compositions with improved cosmetic properties, in particular as regards the feel of the hair or the skin.

The inventors have now found that a cationic polymer defined below, with a weight-average molecular mass of less than 20,000, makes it possible to achieve these aims.

A subject of the invention is thus a cosmetic composition, characterized in that it comprises, in a cosmetically acceptable medium, at least one silicone and at least one polymer or copolymer comprising repeating units selected from units of formulae (I) and (II) defined below, with a weight-average molecular mass of less than 20,000.

Another subject of the invention relates to a process for treating keratin substances, such as the hair, involving applying cosmetic compositions according to the invention to the substances.

Various subjects of the invention will now be outlined in detail. All of the meanings and definitions of the compounds used in the present invention given below are valid for all of the subjects of the invention.

For the purposes of the present invention, the expression "cationic polymer" denotes any polymer containing repeating units selected from cationic groups and groups which can be ionized into cationic groups. Thus, copolymers also containing anionic groups will be denoted by the term "cationic polymer".

The compositions in accordance with the invention necessarily comprise at least one cationic polymer or copolymer containing repeating units selected from units corresponding to formulae (I) and (II):

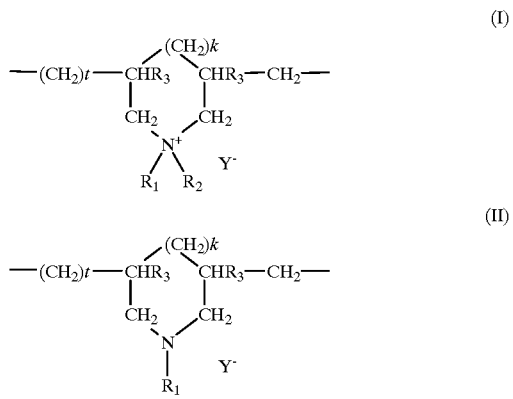

in which:

k and t are equal to 0 or 1, the sum k+t being equal to 1;
$R_3$ denotes a hydrogen atom or a methyl radical;
$R_1$ and $R_2$, independently of each other, denote an alkyl group having from 1 to 22 carbon atoms, a hydroxyalkyl group in which the alkyl group preferably has from 1 to 5 carbon atoms, a lower amidoalkyl group (1 to 5 carbon atoms) or $R_1$ and $R_2$ can denote, together with the nitrogen atom to which they are attached, heterocyclic groups such as piperidyl or morpholinyl; and $Y^-$ is an anion such as bromide, chloride, acetate, borate, citrate, tartrate, bisulphate, sulphate or phosphate.

These polymers can be prepared in particular according to U.S. Pat. Nos. 3,996,146 and 3,288,770, the disclosures of which are specifically incorporated by reference herein.

Preferably, $R_1$ and $R_2$ denote, independently of each other, methyl or ethyl and $R_3$ denotes a hydrogen atom.

The cationic polymers used preferably have a weight-average molecular mass ranging from approximately 5000 to approximately 17,000, and more preferably ranging from approximately 8000 to approximately 15,000.

The weight-average molecular masses are measured by GPC (gel permeation chromatography).

The present invention also relates to copolymers comprising repeating units selected from formulae (I) and (II). The copolymers comprise repeating units resulting from copolymerization with acrylic or methacrylic acid, $C_1$–$C_{12}$ alkyl methacrylates, $C_1$–$C_{12}$ alkyl acrylates or acrylamide.

Among the polymers defined above, mention may be made more particularly of the diallyldimethylammonium chloride homopolymer with a weight-average molecular mass ranging from 9500 to 12,500.

According to the invention, the cationic polymer(s) of low molecular mass can preferably represent from 0.001% to 10% by weight, more preferably from 0.005% to 5% by weight and even more preferably from 0.01 % to 3% by weight, of the total weight of the final composition.

The silicones which can be used in accordance with the invention can be soluble or insoluble in water or in the final composition. They can be volatile or non-volatile.

The silicones which can be used in accordance with the invention are, in particular, organopolysiloxanes which are insoluble in the composition, and can be in the form of oils, waxes, resins or gums.

The organopolysiloxanes are defined in greater detail in the book by Walter Noll "Chemistry and Technology of Silicones" (1968) Academic Press, the disclosure of which is specifically incorporated by reference herein. They can be volatile or non-volatile.

When they are volatile, the silicones are selected more particularly from those having a boiling point ranging from 60° C. to 260° C., and more particularly from:

(i) cyclic silicones containing from 3 to 7 and more preferably 4 to 5 silicon atoms. These are, for example, octamethylcyclotetrasiloxane sold in particular under the name "VOLATILE SILICONE 7207" by Union Carbide or "SILBIONE 70045 V 2" by Rhône-Poulenc, decamethylcyclopentasiloxane sold under the name "VOLATILE SILICONE 7158" by Union Carbide, "SILBIONE 70045 V 5" by Rhône-Poulenc, and mixtures thereof.

Mention may also be made of cyclocopolymers of the dimethylsiloxane/methylalkylsiloxane type, such as "SILICONE VOLATILE FZ 3109" sold by the company Union Carbide, of chemical structure:

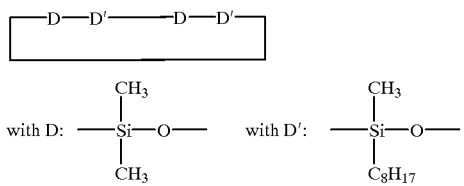

Mention may also be made of mixtures of cyclic silicones with organosilicon-based compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile silicones having from 2 to 9 silicon atoms and having a viscosity of less than or equal to $5 \times 10^{-6}$ m$^2$/s at 25° C. This is, for example, decamethyltetrasiloxane sold in particular under the name "SH 200" by the company Toray Silicone. Silicones forming part of this category are also described in the article published in Cosmetics and Toiletries, Vol. 91, Jan. 1976, p. 27–32—Todd & Byers "Volatile Silicone Fluids for Cosmetics", the disclosure of which is specifically incorporated by reference herein.

Non-volatile silicones are preferably used, and more particularly:
(i) polyalkylsiloxanes;
(ii) polyarylsiloxanes;
(iii) polyalkylarylsiloxanes;
(iv) silicone gums;
(v) silicone resins;
(vi) polyorganosiloxanes containing in their general structure one or more organofunctional groups directly attached to the siloxane chain or attached via a hydrocarbon radical;
(vii) block copolymers having a linear polysiloxane-polyoxyalkylene block as repeating units;
(viii) grafted silicone polymers, with a non-silicone organic skeleton, consisting of an organic main chain formed from organic monomers containing no silicone, on which is grafted, inside the said chain as well as, optionally, on at least one of its ends, at least one polysiloxane macromonomer;
(ix) grafted silicone polymers, with a polysiloxane skeleton grafted with non-silicone organic monomers, comprising a polysiloxane main chain on which is grafted, inside the said chain as well as, optionally, on at least one of its ends, at least one organic macromonomer containing no silicone;
(x) or mixtures thereof.

Among the polyalkylsiloxanes, mention may be made mainly of:
linear polydimethylsiloxanes containing trimethylsilyl end groups, such as, for example, and in a non-limiting manner, the SILBIONE oils of the series 70047 sold by Rhône-Poulenc, the oil 47 V 500,000 from Rhône-Poulenc or certain VISCASIL products from General Electric;

linear polydimethylsiloxanes containing hydroxydimethylsilyl end groups, such as the oils of the series 48 V from Rhône-Poulenc.

In this class of polyalkylsiloxanes, mention may also be made of the polyalkylsiloxanes sold by the company Goldschmidt under the trade names ABIL WAX 9800 and ABIL WAX 9801, which are poly($C_1$–$C_{20}$)alkylsiloxanes.

Among the polyalkylarylsiloxanes, mention may be made of linear or branched polydimethylmethylphenylsiloxanes or polydimethyidiphenylsiloxanes, such as the product DC 556 COSMETIC GRADE FLUID from Dow Corning.

The silicone gums, in accordance with the invention, are polyorganosiloxanes with a number-average molecular mass preferably ranging from 200,000 to 1,000,000, which are used alone or as a mixture in a solvent. This solvent can be selected from volatile silicones, polydimethylsiloxane (PDMS) oils, polyphenylmethylsiloxane (PPMS) oils, isoparaffins, polyisobutylenes, methylene chloride, pentane, dodecane and tridecanes, or mixtures thereof.

Mention is made, for example, of the following compounds:
polydimethylsiloxane,
poly[(dimethylsiloxane)/(methylvinylsiloxane)],
poly[(dimethylsiloxane)/(diphenylsiloxane)],
poly[(dimethylsiloxane)/(phenylmethylsiloxane)],
poly[(dimethylsiloxane)/(diphenylsiloxane)/(methylvinylsiloxane)].

Mention may be made, for example, of the following mixtures:

1) mixtures formed from a polydimethylsiloxane which is hydroxylated at the end of the chain (Dimethiconol according to the CTFA nomenclature) and of a cyclic polydimethylsiloxane (Cyclomethicone according to the CTFA nomenclature), such as the product Q2 1401 sold by the company Dow Corning;

2) mixtures formed from a polydimethylsiloxane gum with a cyclic silicone, such as the product SF 1214 SILICONE FLUID from General Electric, which is an SE 30 gum of molecular weight 500,000, dissolved in SF 1202 SILICONE FLUID (decamethylcyclopentasiloxane);

3) mixtures of two polydimethylsiloxanes (PDMS) of different viscosity, in particular of a PDMS gum and of a PDMS oil, such as the products SF 1236 and CF 1241 from General Electric. The product SF 1236 is a mixture of an oil SE 30 defined above, with a viscosity of 20 m$^2$/s, and of an oil SF 96 of viscosity $5 \times 10^{-5}$ m$^2$/s (15% SE 30 gum and 85% SF 96 oil). The product CF 1241 is a mixture of an SE 30 gum (33%) and a PDMS (67%) of viscosity $10^{-3}$ m$^2$/s.

The silicone resins in accordance with the invention are preferably crosslinked siloxane systems containing the units: $R_2SiO_{2/2}$, $RSiO_{3/2}$, and $SiO_{4/2}$ in which R denotes a hydrocarbon group having from 1 to 6 carbon atoms or a phenyl group. Among these products, those particularly preferred are those in which R denotes a lower alkyl radical or a phenyl radical.

Among these resins, mention may be made of the product sold under the name DOW CORNING 593 by Dow Corning, or those sold under the name SILICONE FLUID SS 4267 by General Electric, and which are dimethyl/trimethylpolysiloxanes.

The organomodified polyorganosiloxanes of the invention are polysiloxanes as defined above, containing in their general structure one or more organofunctional groups directly attached to the siloxane chain or attached via a hydrocarbon radical.

Mention is made, for example, of polysiloxanes containing:

a) polyethylenoxy and/or polypropylenoxy groups, optionally containing alkyl groups, such as the product known as laurylmethicone copolyol, sold under the name Q2 5200 by Dow Corning;

b) (per)fluoro groups, for instance trifluoroalkyl groups such as, for example, those sold by SHIN ETSU under the name FL 100;

c) thiol groups;

d) carboxylate groups, such as the products described in European patent EP 185,507, the disclosure of which is specifically incorporated by reference herein, from Chisso Corporation;

e) hydroxyl-containing groups, such as polyorganopolysiloxanes containing a hydroxyalkyl function, described in French patent application FR 85/16334, the disclosure of which is specifically incorporated by reference herein, and in particular polyorganopolysiloxanes containing a Y-hydroxypropyl function;

f) alkoxy-containing groups containing at least 12 carbon atoms, such as the product SILICONE COPOLYMER F755 from SWS Silicones, and the products ABIL WAX 2428, ABIL WAX 2434 and ABIL WAX 2440 from the company Goldschmidt;

g) acyloxyalkyl groups containing at least 12 carbon atoms, such as the polyorganosiloxanes described in French patent application FR 88/17433, the disclosure of which is specifically incorporated by reference herein, and in particular polyorganosiloxanes containing a stearoyloxypropyl function;

h) amphoteric groups;

l) bisulphite groups;

j) hydroxyacylamino groups, such as the polyorganosiloxanes described in European patent application EP 342,834 the disclosure of which is specifically incorporated by reference herein,. Mention may be made, for example, of the product Q2 8413 from the company Dow Corning;

k) substituted or unsubstituted amine groups, such as the products sold under the name GP 4 SILICONE FLUID and GP 7100 by the company Genesee or the products sold under the names Q2 8220 and DOW CORNING 929 or 939 by the company Dow Corning. The substituted amine groups are, in particular, $C_1$–$C_4$ aminoalkyl groups; the silicones known as amodimethicone and trimethylsilylamodimethicone according to the CTFA name are used more particularly.

The block copolymers having a linear polysiloxane-polyoxyalkylene block as repeating units, which are used in the context of the present invention, preferably have the following general formula:

$$([Y(R_2SiO)_a R'_2SiYO][C_nH_{2n}O)_b]_c \quad (V)$$

in which:

R and R' independently represent a monovalent hydrocarbon radical containing no aliphatic unsaturation, n is an integer ranging from 2 to 4, a is an integer preferably greater than or equal to 5, more preferably ranging from 5 and 200 and even more particularly ranging from 5 to 100, b is an integer preferably greater than or equal to 4, more preferably ranging from 4 to 200 and even more particularly ranging from 5 to 100, c is an integer preferably greater than or equal to 4, more preferably ranging from 4 to 1000 and even more particularly ranging from 5 to 300, Y represents a divalent organic group which is attached to the adjacent silicon atom via a carbon-silicon bond and to a polyoxyalkylene block via an oxygen atom, the average molecular weight of each siloxane block preferably ranges from about 400 to about 10,000, that of each polyoxyalkylene block preferably ranges from about 300 to about 10,000, the siloxane blocks represent from about 10% to about 95% by weight of the block copolymer, the weight-average molecular weight of the block copolymer preferably is at least 3000 and more preferably ranging from 5000 to 1,000,000 and even more particularly ranges from 10,000 to 200,000.

R and R' are preferably selected from the group comprising alkyl radicals such as, for example, methyl, ethyl, propyl, butyl, pentyl, hexyl, octyl, decyl and dodecyl radicals, aryl radicals such as, for example, phenyl and naphthyl radicals, aralkyl radicals such as, for example, benzyl and phenylethyl radicals, and tolyl, xylyl and cyclohexyl radicals.

Y is preferably —R"—, —R"—CO—, —R"—NHCO—, —R"—NH—CO—NH—R'"—NHCO, —R"—OCONH—R'"—NHCO—, where R" is a divalent alkylene group such as, for example, ethylene, propylene or butylene and R'" is a divalent alkylene group or a divalent arylene group such as —$C_6H_4$—, —$C_6H_4$—$C_6H_4$—, —$C_6H_4$—$CH_2$—$C_6H_4$–, —$C_6H_4$—$C(CH_3)_2$—$C_6H_4$–.

Even more preferably, Y represents a divalent alkylene radical, more particularly the —$CH_2$—$CH_2$—$CH_2$— radical or the $C_4H_8$ radical.

The preparation of the block copolymers used in the context of the present invention is described in European patent application EP 0,492,657 A1, the teaching of which is specifically included in the present description by way of reference.

The polymers with a non-silicone organic skeleton grafted with monomers containing a polysiloxane, in accordance with the invention, are more preferably selected from those described in U.S. Pat. Nos. 4,693,935, 4,728,571 and 4,972,037 and patent applications EP-A-0,412,704, EP-A-0,412,707, EP-A-0,640,105 and WO 95/00578, the teachings of which are specifically included in the present description, in their entirety, by way of non-limiting references. These are copolymers obtained by radical polymerization from monomers containing ethylenic unsaturation and from silicone macromers having a terminal vinyl group, or alternatively they are copolymers obtained by reaction of a polyolefin comprising functionalized groups and of a polysiloxane macromer having a terminal function which is reactive with the functionalized groups.

Examples of polymers with a polysiloxane skeleton grafted with non-silicone organic monomers, which are suitable for carrying out the present invention, as well as the specific method for preparing them, are described in particular in patent applications EP-A-0,582,152, WO 93/23009 and WO 95/03776, the teachings of which are specifically included in the present description, in their entirety, by way of non-limiting references.

According to the invention, all the silicones can also be used in the form of emulsions or microemulsions.

The silicones which are particularly preferred in accordance with the invention are:

non-volatile silicones selected from the family of polyalkylsiloxanes containing trimethylsilyl terminal groups, such as oils having a viscosity ranging from 0.2 to 2.5 m²/s at 25° C., such as the oils of the series DC200 from Dow Corning, in particular the oil of viscosity 60,000 cSt, of the series SILBIONE 70047 and 47 and more particularly the oil 70 047 V 500,000 sold by the company Rhône-Poulenc, polyalkylsiloxanes containing dimethylsilanol terminal groups, such as dimethiconol or polyalkylarylsiloxanes such as the oil SILBIONE 70641 V 200 sold by the company Rhône-Poulenc;

mixtures of organopolysiloxanes and of cyclic silicones, such as the product Q2 1401 sold by the company Dow Corning, and the product SF 1214 sold by the company General Electric;

mixtures of two PDMSs of different viscosities, in particular of a gum and an oil, such as the product SF 1236 sold by the company General Electric;

the organopolysiloxane resin sold under the name DOW CORNING 593;

polysiloxanes containing amine groups, such as amodimethicones or trimethylsilylamodimethicones.

According to the invention, the silicone(s) can represent preferably from 0.001% to 10% by weight, more preferably from 0.005% to 5% by weight and even more preferably from 0.01% to 3% by weight, of the total weight of the final composition.

The compositions of the invention also advantageously contain at least one surfactant which is generally present in an amount ranging from approximately 0.1% to approximately 60% by weight, more preferably from 3% to 40% and even more preferably from 5% to 30%, relative to the total weight of the composition.

This surfactant can be selected from anionic, amphoteric, nonionic or cationic surfactants, or mixtures thereof.

The surfactants which are suitable for carrying out the present invention are, in particular, the following:

(i) Anionic surfactant(s):

In the context of the present invention, their nature is not of truly essential importance.

Thus, as examples of anionic surfactants which can be used, alone or as mixtures, in the context of the present invention, mention may be made in particular (non-limiting list) of salts (in particular alkaline salts, especially sodium salts, ammonium salts, amine salts, amino alcohol salts or magnesium salts) of the following compounds: alkyl sulphates, alkyl ether sulphates, alkylamido ether sulphates, alkylarylpolyethersulphates, monoglyceride sulphates; alkyl sulphonates, alkyl phosphates, alkylamide sulphonates, alkylaryl sulphonates, α-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates and N-acyl taurates, the alkyl or acyl radical of all of these various compounds preferably containing from 6 to 24 carbon atoms, and the aryl radical preferably denoting a phenyl or benzyl group. Among the anionic surfactants which can also be used, mention may also be made of fatty acid salts such as salts of oleic, ricinoleic, palmitic or stearic acid, coconut oil acid or hydrogenated coconut oil acid; acyl lactylates in which the acyl radical contains from 6 to 20 carbon atoms. Mention may also be made of weakly anionic surfactants, such as alkyl D-galactosiduronic acids and their salts, as well as polyoxyalkylenated ($C_6$–$C_{24}$)alkyl ether carboxylic acids, polyoxyalkylenated ($C_6$–$C_{24}$)alkylaryl ether carboxylic acids, polyoxyalkylenated ($C_6$–$C_{24}$)alkylamido ether carboxylic acids and their salts, in particular those containing from 2 to 50 ethylene oxide groups, and mixtures thereof.

Among the anionic surfactants, it is preferred, according to the invention, to use alkyl sulphate salts and alkyl ether sulphate salts and mixtures thereof.

(ii) Nonionic surfactant(s):

The nonionic surfactants are, themselves also, compounds that are well known per se (see in particular in this respect "Handbook of Surfactants" by M. R. Porter, published by Blackie & Son (Glasgow and London), 1991, pp. 116–178) and, in the context of the present invention, their nature is not of essential importance. Thus, they can be selected in particular (non-limiting list) from polyethoxylated, polypropoxylated or polyglycerolated fatty alcohols, α-diols, alkylphenols or acids having a fatty chain containing, for example, from 8 to 18 carbon atoms, it being possible for the number of ethylene oxide or propylene oxide groups to range in particular from 2 to 50 and for the number of glycerol groups to range in particular from 2 to 30. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average from 1 to 5 and in particular from 1.5 to 4 glycerol groups; polyethoxylated fatty amines preferably having from 2 to 30 mol of ethylene oxide, oxyethylenated fatty acid esters of sorbitan having from from 2 to 30 mol of ethylene oxide; fatty acid esters of sucrose, fatty acid esters of polyethylene glycol, alkylpolyglycosides, N-alkylglucamine derivatives, amine oxides such as ($C_{10}$–$C_{14}$)alkylamine oxides or N-acylaminopropylmorpholine oxides. It will be noted that the alkylpolyglycosides constitute nonionic surfactants that are particularly suitable for incorporation into the context of the present invention.

(iii) Amphoteric surfactant(s):

The amphoteric surfactants, whose nature is not of essential importance in the context of the present invention, can be, in particular (non-limiting list), aliphatic secondary or tertiary amine derivatives, in which the aliphatic radical is a straight or branched chain containing from 8 to 22 carbon atoms and containing at least one aqueous-solubilizing anionic group (for example carboxylate, sulphonate, sulphate, phosphate or phosphonate); mention may also be made of ($C_6$–$C_{20}$)alkylbetaines, sulphobetaines, ($C_8$–$C_{20}$) alkyl-amido($C_1$–$C_6$)alkylbetaines or ($C_8$–$C_{20}$)alkylamido ($C_1$–$C_6$)alkylsulphobetaines.

Among the amine derivatives, mention may be made of the products sold under the name MIRANOL, as described in U.S. Pat. Nos. 2,528,378 and 2,781,354, the disclosures of which are specifically incorporated by reference herein, and having the structures:

$$R_2\text{—CONHCH}_2\text{CH}_2\text{—N}(R_3)(R_4)(\text{CH}_2\text{COO—}) \qquad (2)$$

to in which:

$R_2$ denotes an alkyl radical derived from an acid $R_2$—COOH present in hydrolysed coconut oil, a heptyl, nonyl or undecyl radical, $R_3$ denotes a β-hydroxyethyl group and $R_4$ denotes a carboxymethyl group; and

$$R_5\text{—CONHCH}_2\text{CH}_2\text{—N(B)(C)} \qquad (3)$$

in which:

B represents —$CH_2CH_2OX'$,

C represents —$(CH_2)_z$—Y', with z=1 or 2,

X' denotes the —$CH_2CH_2$—COOH group or a hydrogen atom,

Y' denotes —COOH or the —$CH_2$—CHOH—$SO_3H$ radical, $R_5$ denotes an alkyl radical of an acid $R_9$—COOH present in coconut oil or in hydrolysed linseed oil, an alkyl radical, in particular a $C_7$, $C_9$, $C_{11}$ or $C_{13}$ alkyl radical, a $C_{17}$ alkyl radical in its iso form, or an unsaturated $C_{17}$ radical.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, and cocoamphodipropionic acid.

By way of example, mention may be made of cocoamphodiacetate sold under the trade name MIRANOL C2M concentrate by the company Rhône-Poulenc.

In the compositions in accordance with the invention, mixtures of surfactants are preferably used, and in particular mixtures of anionic surfactants and mixtures of anionic surfactants and amphoteric or nonionic surfactants. A particularly preferred mixture is a mixture comprising at least one anionic surfactant and at least one amphoteric surfactant.

An anionic surfactant is preferably used which is selected from sodium, triethanolamine or ammonium ($C_{12}$–$C_{14}$)alkyl sulphates, sodium, triethanolamine or ammonium ($C_{12}$–$C_{14}$) alkyl ether sulphates oxyethylenated with 2.2 mol of ethylene oxide, sodium cocoyl isethionate and sodium α-($C_{14}$–$C_{16}$)olefin sulphonate and mixtures thereof with:

- either an amphoteric surfactant such as the amine derivatives known as disodium cocoamphodipropionate or sodium cocoamphopropionate, sold in particular by the company Rhône-Poulenc under the trade name "MIRANOL C2M CONC" as an aqueous solution containing 38% active material, or under the name Miranol C32;
- or an amphoteric surfactant of zwitterionic type, such as alkylbetaines, in particular the cocobetaine sold under the name "DEHYTON AB 30" as an aqueous solution containing 32% AM, by the company Henkel.

Cationic surfactants can also be used, among which mention may be made, in particular (non-limiting list) of: optionally polyoxyalkylenated salts of primary, secondary or tertiary fatty amines; quaternary ammonium salts such as tetraalkylammonium, alkylamido-alkyltrialkylammonium, trialkylbenzylammonium, trialkylhydroxyalkylammonium or alkylpyridinium chlorides or bromides; imidazoline derivatives; or amine oxides of cationic nature.

The compositions of the invention can also contain at least one additive selected from thickeners, surfactants, fragrances, pearlescent agents, preserving agents, sunscreens, proteins, vitamins, polymers, plant, animal, mineral or synthetic oils and any other additive conventionally used in the cosmetics field.

These additives are present in the composition according to the invention in proportions which can preferably range from 0 to 50% by weight relative to the total weight of the composition. The precise amount of each additive is readily determined by a person skilled in the art depending on its nature and its function.

The compositions in accordance with the invention can be used more particularly for washing or treating keratin substances, such as the hair, the skin, the eyelashes, the eyebrows, the nails, the lips or the scalp, and more particularly the hair.

In particular, the compositions according to the invention are detergent compositions such as shampoos, shower gels and bubble baths. In this embodiment of the invention, the compositions comprise a washing base, which is generally aqueous.

The surfactant(s) forming the washing base can be selected, indifferently, alone or as mixtures, from anionic, amphoteric, nonionic and cationic surfactants as defined above.

The quantity and quality of the washing base are those which are sufficient to give the final composition satisfactory foaming power and/or detergent power.

Thus, according to the invention, the washing base can represent preferably from 2% to 50% by weight, more preferably from 10% to 35% by weight and even more preferably from 12% to 25% by weight, of the total weight of the final composition.

The subject of the invention is also a process for treating keratin substances, such as the skin or the hair, characterized in that it consists in applying a cosmetic composition as defined above to the keratin substances and then optionally in rinsing with water.

Thus, this process according to the invention makes it possible to maintain the hairstyle and to treat, care for, wash or remove make-up from the skin, the hair or any other keratin substance.

The compositions of the invention can also be in the form of a rinse-out or leave-in conditioner, in the form of compositions for permanent-waving, straightening, dyeing or bleaching the hair or alternatively in the form of rinse-out compositions to be applied before or after dyeing, bleaching, permanent-waving or straightening the hair or alternatively between the two steps of a permanent-waving or straightening operation on the hair.

The compositions of the invention can also be in the form of washing compositions for the skin, and in particular in the form of bath or shower solutions or gels or in the form of make-up-removing products.

The compositions according to the invention can also be in the form of aqueous or aqueous-alcoholic lotions to care for the skin and/or the hair.

The cosmetic compositions according to the invention can be in the form of a gel, a milk, a cream, an emulsion, a thickened lotion or a foam and can be used for the skin, the nails, the eyelashes, the lips and, more particularly, the hair.

The compositions can also be hairsetting lotions, blow-drying lotions, fixing compositions (lacquers) or styling compositions. The lotions can be packaged in various forms, in particular in vaporizers, pump-dispenser bottles or in aerosol containers in order to ensure application of the composition in vaporized form or in the form of a foam. Such packaging forms are indicated, for example, when it is desired to obtain a spray, a lacquer or a foam for fixing or treating the hair.

The compositions can also be make-up compositions such as foundations, tinted day creams, mascaras, blushers, eyeshadows, lip compositions or nail varnishes.

In all of the text hereinabove and hereinbelow, the percentages are expressed on a weight basis.

The invention will now be illustrated more fully with the aid of the following examples, which should not be considered as limiting it to the embodiments described.

In the examples, AM means active material.

EXAMPLE 1

Two shampoo compositions, one in accordance with the invention (composition A) and the other a comparative composition (composition B), were prepared:

|  | A<br>Invention | B<br>Comparative |
|---|---|---|
| Sodium lauryl ether sulphate (70/30 $C_{12}/C_{14}$) containing 2.2 mol of ethylene oxide (AM = active material) | 15.5 g AM | 15.5 g AM |
| Disodium cocoamphodiacetate (*) | 2.56 g AM | 2.56 g AM |
| Aminosilicone (***) | 1.05 g AM | 1.05 g AM |
| Silicone (60,000 cSt) (****) | 2 g | 2 g |
| Diallyldimethylammonium chloride homopolymer of Mw ≈ 11,000 | 0.6 g | — |
| Diallyldimethylammonium chloride homopolymer of Mw ≈ 400,000 (Merquat 100 from Calgon) | — | 0.6 g |
| Ethylene glycol distearate | 1.5 g | 1.5 g |
| Crosslinked polyacrylic acid (**) | 0.2 g | 0.2 g |
| Coconut acid monoisopropanolamide | 0.9 g | 0.9 g |
| Citric acid qs pH | 5 | 5 |
| Demineralized water qs | 100 g | 100 g |

(*) MIRANOL C2M sold by Rhône-Poulenc
(**) CARBOPOL 980 sold by Goodrich
(***): Amodimethicone sold as a cationic emulsion containing 35% active material, under the name FLUID DC 939 by the company Dow Corning
(****): Polydimethylsiloxane of viscosity 60,000 cSt, sold by the company Dow Corning under the name FLUID DC 200 - 60,000 cSt.

Shampooing was carried out by applying about 12 g of composition A to natural hair which was made wet beforehand. The shampoo was worked into a lather and was then rinsed thoroughly with water.

The process was carried out according to the same procedure as above with the comparative composition B.

A panel of experts evaluated the disentangling and the feel of the hair when wet, and the disentangling, the feel, the lightness, the softness and the smoothness of the hair when dried.

Hair treated with composition A felt natural and light, whereas hair treated with composition B containing a polymer of the same structure but of high molecular mass had a lank feel. The hair did not seem clean.

EXAMPLE 2

A shampoo of the following composition was prepared:

| | | |
|---|---|---|
| Sodium lauryl ether sulphate (70/30 $C_{12}/C_{14}$) containing 2.2 mol of ethylene oxide, as an aqueous solution containing 70% AM (AM = active material) | 15.5 g | AM |
| Disodium cocoamphodiacetate (*) | 2.56 g | AM |
| Polydimethylsiloxane as an aqueous emulsion containing 50% AM (***) | 2.7 g | |
| Diallyldimethylammonium chloride homopolymer of Mw ≈ 11,000 | 0.6 g | |
| Ethylene glycol distearate | 1.5 g | |
| Coconut acid monoisopropanolamide | 0.9 g | |
| Crosslinked polyacrylic acid (**) | 0.2 g | |
| Citric acid qs | pH 5 | |
| Fragrance, preserving agents | qs | |
| Demineralized water qs | 100 g | |

(*) MIRANOL C2M sold by Rhône-Poulenc
(**) CARBOPOL 980 sold by Goodrich
(***): Polydimethylsiloxane (60,000 cSt) as a nonionic emulsion containing 50% active material, sold under the name DC 2-1691 by the company Dow Corning.

EXAMPLE 3

A shampoo of the following composition was prepared:

| | | |
|---|---|---|
| Sodium lauryl ether sulphate (70/30 $C_{12}/C_{14}$) containing 2.2 mol of ethylene oxide, as an aqueous solution containing 70% AM (AM = active material) | 15.5 g | AM |
| Cocobetaine containing 32% AM (*) | 3.2 g | AM |
| Aminosilicone (***) | 1.05 g | |
| Silicone (60,000 cSt) (****) | 2 g | |
| Diallyldimethylammonium chloride homopolymer of Mw ≈ 11,000 | 0.6 g | |
| Quaternized wheat protein hydrolysate | 0.1 g | AM |
| Ethylene glycol mono- and di-stearate | 1.5 g | |
| Coconut acid monoisopropanolamide | 1 g | |
| Crosslinked polyacrylic acid (**) | 0.2 g | |
| Citric acid qs | pH 5 | |
| Fragrance, preserving agents | qs | |
| Demineralized water qs | 100 g | |

(*) DEHYTON AB 30 from Henkel
(**) CARBOPOL 980 sold by Goodrich
(***): Amodimethicone sold as a cationic emulsion containing 35% active material, under the name FLUID DC 939 by the company Dow Corning
(****): Polydimethylsiloxane of viscosity 60,000 cSt, sold by the company Dow Corning under the name FLUID DC 200 - 60,000 cSt.

We claim:

1. A cosmetic composition comprising, in a cosmetically acceptable medium, at least one silicone and at least one cationic polymer selected from polymers and copolymers containing repeating units selected from formulae (I) and (II) units:

$$-(CH_2)_t-CHR_3\underset{CH_2}{\overset{(CH_2)_k}{\diagup}}CHR_3-CH_2- \quad (I)$$

$$\underset{R_1\ R_2}{\overset{N^+\ Y^-}{\diagdown}}$$

$$-(CH_2)_t-CHR_3\underset{CH_2}{\overset{(CH_2)_k}{\diagup}}CHR_3-CH_2- \quad (II)$$

$$\underset{R_1}{\overset{N\ Y^-}{\diagdown}}$$

in which:
k and t are equal to 0 or 1, wherein the sum k+t is 1;
$R_3$ denotes a hydrogen atom or a methyl radical;
$R_1$ and $R_2$ independently denote an alkyl group having from 1 to 22 carbon atoms, a hydroxyalkyl group in which the alkyl group has from 1 to 5 carbon atoms, a lower amidoalkyl group having from 1 to 5 carbon atoms or $R_1$ and $R_2$ can denote, together with the nitrogen atom to which they are attached, a heterocyclic group;

Y⁻ is an anion, wherein the weight-average molecular mass of said cationic polymer is less than 20,000.

2. A cosmetic composition according to claim 1, wherein at least one of the following is true:

said heterocyclic group is piperidyl or morpholinyl; and

Y⁻ is selected from bromide, chloride, acetate, borate, citrate, tartrate, bisulphate, bisulphite, sulphate and phosphate.

3. A cosmetic composition according to claim 1, wherein $R_1$ and $R_2$ independently denote methyl or ethyl and $R_3$ denotes a hydrogen atom.

4. A cosmetic composition according to claim 1, wherein said at least one cationic polymer is selected from dimethyidiallylammonium chloride homopolymers with a weight-average molecular mass ranging from 9500 to 12,500.

5. A cosmetic composition according to claim 1, wherein said weight-average molecular mass ranges from 5000 and 17,000.

6. A cosmetic composition according to claim 5, wherein said weight-average molecular mass ranges from 8000 to 15,000.

7. A cosmetic composition according to claim 1, wherein at least one silicone is selected from:

(i) polyalkylsiloxanes;

(ii) polyarylsiloxanes;

(iii) polyalkylarylsiloxanes;

(iv) silicone gums;

(v) silicone resins;

(vi) polyorganosiloxanes containing in their general structure one or more organofunctional groups directly attached to the siloxane chain or attached via a hydrocarbon radical;

(vii) block copolymers having a linear polysiloxane-polyoxyalkylene block as repeating units;

(viii) grafted silicone polymers, with a non-silicone organic skeleton, comprising an organic main chain formed from organic monomers containing no silicone, on which is grafted, inside said chain as well as, optionally, on at least one of its ends, at least one polysiloxane macromonomer; and (ix) grafted silicone polymers, with a polysiloxane skeleton grafted with non-silicone organic monomers, comprising a polysiloxane main chain on which is grafted, inside said chain as well as, optionally, on at least one of its ends, at least one organic macromonomer containing no silicone.

8. A cosmetic composition according to claim 1, wherein said cosmetic composition further comprises at least one surfactant.

9. A cosmetic composition according to claim 8, wherein said at least one surfactant is selected from anionic, cationic, nonionic and amphoteric surfactants.

10. A cosmetic composition according to claim 8, wherein said at least one surfactant is present in an amount ranging from 0.1% to 60% by weight, relative to the total weight of said composition.

11. A cosmetic composition according to claim 10, wherein said at least one surfactant is present in an amount ranging from 3% to 40% by weight, relative to the total weight of said composition.

12. A cosmetic composition according to claim 11, wherein said at least one surfactant is present in an amount ranging from 5% to 30% by weight, relative to the total weight of said composition.

13. A cosmetic composition according to claim 1, wherein said at least one cationic polymer is present in an amount ranging from 0.001% to 10% by weight relative to the total weight of said composition.

14. A cosmetic composition according to claim 13, wherein said at least one cationic polymer is present in an amount ranging from 0.005% to 5% by weight relative to the total weight of said composition.

15. A cosmetic composition according to claim 14, wherein said at least one cationic polymer is present in an amount ranging from 0.01% to 3% by weight relative to the total weight of said composition.

16. A cosmetic composition according to claim 1, wherein said at least one silicone is present in an amount ranging from 0.001% to 10% by weight relative to the total weight of said composition.

17. A cosmetic composition according to claim 16, wherein said at least one silicone is present in an amount ranging from 0.005% to 5% by weight relative to the total weight of said composition.

18. A cosmetic composition according to claim 17, wherein said at least one silicone is present in an amount ranging from 0.01% to 3% by weight relative to the total weight of said composition.

19. A cosmetic composition according to claim 1, wherein said cosmetic composition further comprises at least one additive.

20. A cosmetic composition according to claim 1, wherein said cosmetic composition is in the form of a shampoo, a conditioner, a composition for permanent-waving, straightening, dyeing or bleaching the hair, a rinse-out composition to be applied between the two steps of a permanent-waving or straightening operation on the hair, or a washing composition for the body.

21. A cosmetic composition according to claim 1, wherein said cosmetic composition is in the form of a hairsetting lotion, a blow-drying lotion, a fixing composition or a styling composition.

22. A cosmetic composition according to claim 1, wherein said cosmetic composition is in the form of a gel, a milk, a cream, an emulsion, a thickened lotion, or a foam.

23. A method of washing a keratin substance comprising applying to said keratin substance an effective amount of at least one cosmetic composition comprising, in a cosmetically acceptable medium, at least one silicone and at least one cationic polymer selected from polymers and copolymers containing repeating units selected from formulae (I) and (II) units:

$$-(CH_2)t-CHR_3 \underset{CH_2}{\overset{(CH_2)k}{\diagup\diagdown}} CHR_3-CH_2- \quad (I)$$
$$\underset{R_1 \quad R_2}{\overset{N^+}{\diagup\diagdown}} Y^-$$

$$-(CH_2)t-CHR_3 \underset{CH_2}{\overset{(CH_2)k}{\diagup\diagdown}} CHR_3-CH_2- \quad (II)$$
$$\underset{R_1}{\overset{N}{|}} Y^-$$

in which:

k and t are equal to 0 or 1, wherein the sum k+t is 1;

$R_3$ denotes a hydrogen atom or a methyl radical;

$R_1$ and $R_2$ independently denote an alkyl group having from 1 to 22 carbon atoms, a hydroxyalkyl group in which the alkyl group has from 1 to 5 carbon atoms, a lower amidoalkyl group having from 1 to 5 carbon atoms or $R_1$ and $R_2$ can denote, together with the nitrogen atom to which they are attached, a heterocyclic group;

$Y^-$ is an anion, wherein the weight-average molecular mass of said cationic polymer is less than 20,000.

24. A method according to claim 23, wherein said keratin substance is hair.

25. A process for treating a keratin substance comprising applying to said keratin substance at least one cosmetic composition comprising, in a cosmetically acceptable medium, at least one silicone and at least one cationic polymer selected from polymers and copolymers containing repeating units selected from formulae (I) and (II) units:

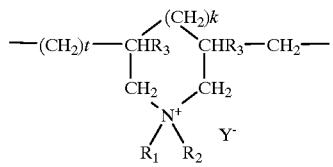

(I)

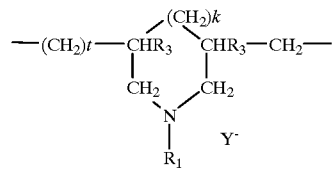

(II)

in which:

k and t are equal to 0 or 1, wherein the sum k+t is 1;

$R_3$ denotes a hydrogen atom or a methyl radical;

$R_1$ and $R_2$ independently denote an alkyl group having from 1 to 22 carbon atoms, a hydroxyalkyl group in which the alkyl group has from 1 to 5 carbon atoms, a lower amidoalkyl group having from 1 to 5 carbon atoms or $R_1$ and $R_2$ can denote, together with the nitrogen atom to which they are attached, a heterocyclic group;

$Y^-$ is an anion, wherein the weight-average molecular mass of said cationic polymer is less than 20,000.

26. A process according to claim 24, wherein said keratin substance is hair.

* * * * *

UNITED STATES PATENT AND TRADEMARK OFFICE
CERTIFICATE OF CORRECTION

PATENT NO.: 6,162,424

DATED: December 19, 2000

INVENTOR(S): DECOSTER et al.

It is certified that an error appears in the above-identified patent and that said Letters Patent is hereby corrected as shown below:

In claim 4, column 13, lines 14-15, "dimethyidiallylammonium" should read -- dimethyldiallylammonium--.

Signed and Sealed this

Twenty-ninth Day of May, 2001

*Attest:*

NICHOLAS P. GODICI

*Attesting Officer*      *Acting Director of the United States Patent and Trademark Office*